(12) United States Patent
Dlubala

(10) Patent No.: US 8,455,509 B2
(45) Date of Patent: Jun. 4, 2013

(54) METHOD FOR THE PREPARATION OF MORPHINE COMPOUNDS

(75) Inventor: Alain Dlubala, Paris (FR)

(73) Assignee: Sanofi, Paris (FR)

(*) Notice: Subject to any disclaimer, the term of this patent is extended or adjusted under 35 U.S.C. 154(b) by 374 days.

(21) Appl. No.: 12/774,156

(22) Filed: May 5, 2010

(65) Prior Publication Data
US 2010/0256176 A1    Oct. 7, 2010

Related U.S. Application Data

(63) Continuation of application No. PCT/FR2008/001558, filed on Nov. 6, 2008.

(60) Provisional application No. 61/021,949, filed on Jan. 18, 2008.

(30) Foreign Application Priority Data

Nov. 9, 2007 (FR) ..................... 07 58923

(51) Int. Cl.
*A61K 31/485*    (2006.01)
*C07D 489/08*   (2006.01)

(52) U.S. Cl.
USPC ............................. 514/282; 546/45

(58) Field of Classification Search
CPC ............................ A61K 31/485; C07D 489/08
USPC ........................... 514/282; 546/45
See application file for complete search history.

(56) References Cited

U.S. PATENT DOCUMENTS 7,851,482 B2 * 12/2010 Dung et al. ................... 514/282
2006/0111383 A1    5/2006 Casner et al.

FOREIGN PATENT DOCUMENTS

| WO | WO 2006/084389 | 8/2006 |
| WO | WO 2006/084412 | 8/2006 |
| WO | WO 2006/094672 | 9/2006 |
| WO | WO 2007/062184 | 5/2007 |
| WO | WO 2007/103105 | 9/2007 |

OTHER PUBLICATIONS

Weiss, U., Derivatives of Morphine. II. Demethylation of 14-Hydroxycodeinone. 14-Hydroxymorphinone and 8,14-Dihydroxydihydromorphinone. Journal of Organic Chemistry, vol. 22. pp. 1505-1508, (1957).
Kotick, M. P., et al., 8-Beta-Substituted Dihydrocodeinones Having Heteroatoms in The Side Chain (1), J. Heterocylic Chem., vol. 18, pp. 1029-1033. (1981).

* cited by examiner

*Primary Examiner* — Charanjit Aulakh
(74) *Attorney, Agent, or Firm* — Scully, Scott, Murphy & Presser, P.C.

(57) ABSTRACT

The present invention relates to a method for the preparation of morphine compounds comprising a low content of $\alpha,\beta$-unsaturated compounds, which comprises the steps of: (i) bringing the crude morphine compound into contact with a base, at a pH of greater than 13, under conditions which make possible the Michael addition reaction on the $\alpha,\beta$-unsaturated compound(s) present; (ii) separating the morphine compound from the reaction mixture; and (iii) if appropriate, separating the addition product formed from the morphine compound. It also relates to a composition comprising at least 99% by dry weight of morphine compound or of a pharmaceutically acceptable salt thereof, and an $\alpha,\beta$-unsaturated compound in a content of less than 100 ppm.

19 Claims, 2 Drawing Sheets

METHOD FOR THE PREPARATION OF MORPHINE COMPOUNDS

Figure 1:
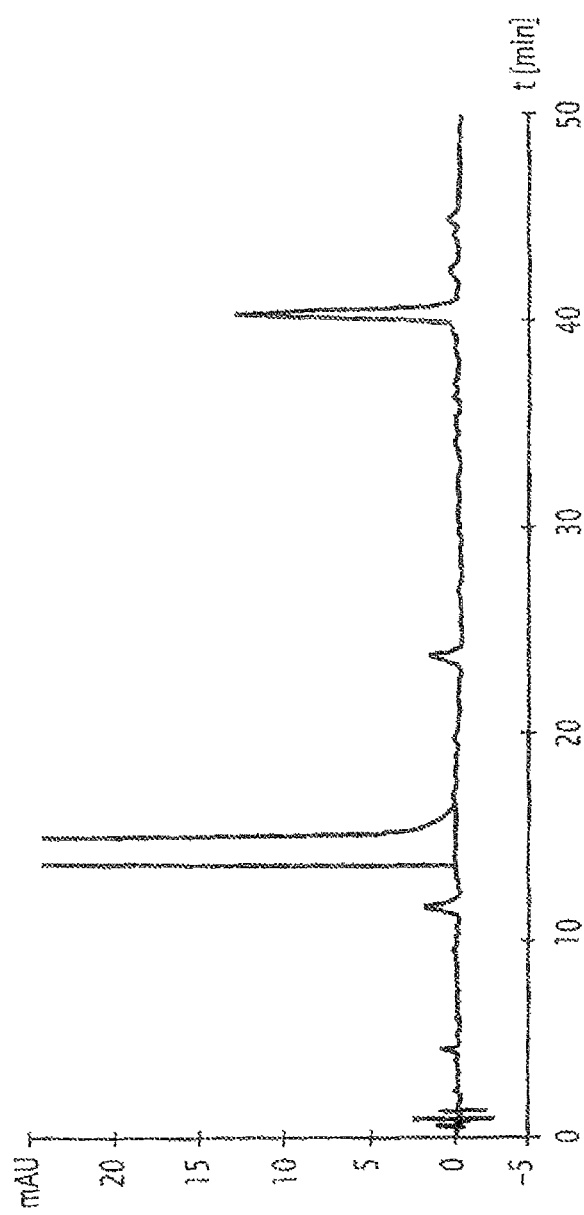

This application is a continuation of International application No. PCT/FR2008/001,558, filed Nov. 6, 2008, which is incorporated herein by reference in its entirety; which claims the benefit of U.S. Provisional Application No. 61/021,949, filed Jan. 18, 2008 and benefit of priority of French patent application Ser. No. 07/58,923, filed Nov. 9, 2007.

The present invention relates to a process for the preparation of morphine compounds, in particular naloxone, comprising a low content of α,β-unsaturated compounds. The present invention also relates to the compositions obtained therefrom.

Morphine and analogous compounds, such as codeine, hydrocodone, hydromorphone, naloxone, naltrexone, oxycodone and oxymorphone, are used as active principles in analgesics.

Naloxone base (CAS No. 465-65-5) is a morphine derivative used as pharmaceutical active principle, in particular for overdose treatment: naloxone is administered to displace morphine from the receptors in order to halt its action.

This compound is accessible by total synthesis but, given the complexity of the molecule, the synthesis generally begins from plant extracts, in particular extracts of the poppy, either starting from the capsule or starting from the resin (opium). These extracts usually comprise different structurally similar compounds which give rise, during the synthesis, to the formation of entities which are sometimes difficult to separate.

In particular, attempts are being made to limit, in morphine compounds, the presence of α,β-unsaturated ketone compounds, due to the supposed toxicity of some of them. Preferably, morphine compounds exhibit a content of α,β-unsaturated compounds of less than 100 ppm.

The document WO 2006/084389 provides for the reduction of the content of α,β-unsaturated compounds by selective hydrogenation. In this context, the document WO 2006/084412 recommends converting the hydroxyl β-ketone group beforehand to a leaving group with acetic anhydride and then selectively hydrogenating it. Furthermore, the document US 2006/0111383 provides for the acidification of the mixture to a pH of less than 6 and for the optional heating of it above 55° C. before hydrogenation.

However, hydrogenation generally involves the use of catalysts, the complete absence of which in the final product is subsequently very difficult to ensure.

The document WO 2007/062184 provides for the removal of α,β-unsaturated electrophilic compounds from oxycodone by reaction with a thiol.

The document WO 2007/103105 also uses a reaction with a thiol to remove the α,β-unsaturated compounds.

The use of a thiol is accompanied by significant odours and by toxicity for most of them. Furthermore, it is also necessary to make sure of the absence of the thiol in the active product.

The aim of the present invention is to provide a process for the preparation of morphine compounds of high purity comprising in particular a low content of α,β-unsaturated compounds.

This aim is achieved by the process according to the invention, which comprises a stage of treatment of the crude product in a basic medium under conditions capable of resulting in the 1,4-addition to the conjugated ketone, also known as Michael addition.

Consequently, according to a first aspect, the invention is targeted at a process for the preparation of morphine compounds comprising a low content of α,β-unsaturated compounds, comprising the stages of:
(i) bringing the crude morphine compound into contact with a base, at a pH of greater than 13, under conditions which make possible the Michael addition reaction on the α,β-unsaturated compound(s) present;
(ii) separating the morphine compound from the reaction mixture; and
(iii) if appropriate, separating the addition product formed from the morphine compound.

According to a second aspect, the invention is targeted at a composition comprising at least 99%, preferably at least 99.5%, by dry weight of morphine compound or one of its pharmaceutically acceptable salts and an α,β-unsaturated compound in a content of less than 100 ppm and preferably of less than 50 ppm.

Definitions

In the account which follows, the expression "morphine compounds" is understood to mean compounds with a structure similar to that of morphine and comprising in particular a phenol ring. These compounds can differ from morphine in particular by the nature of their substituents and by the nature of the bonds. More specifically, they are 3-hydroxymorphinone derivatives corresponding to the following formula (I):

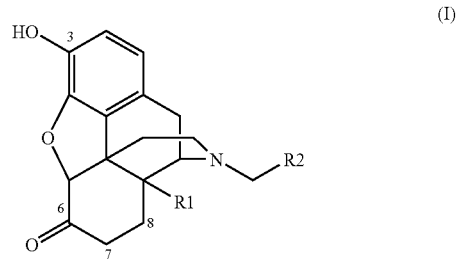

in which:
R1 represents a hydrogen atom or a hydroxyl group and
R2 represents a hydrogen atom or a $(C_1\text{-}C_6)$alkyl, cyclo$(C_3\text{-}C_6)$alkyl or $(C_2\text{-}C_6)$alkenyl group.

In the context of the present invention:
a $(C_1\text{-}C_6)$alkyl group is understood to mean a saturated, linear or branched, aliphatic group comprising between 1 and 6 carbon atoms. Mention may be made, by way of example, of the methyl, ethyl, propyl, isopropyl, butyl, isobutyl, tert-butyl and pentyl groups and the like;
a cyclo$(C_3\text{-}C_6)$alkyl group is understood to mean a cyclic alkyl group comprising between 3 and 6 carbon atoms. Mention may be made, by way of example, of the cyclopropyl, cyclobutyl, cyclopentyl and cyclohexyl groups,
a $(C_2\text{-}C_6)$alkenyl group is understood to mean a mono- or polyunsaturated, linear or branched, aliphatic group comprising, for example, one or two ethylenic unsaturations and comprising between 2 and 6 carbon atoms. Mention may be made, by way of example, of the vinyl group.

Hydromorphone, naloxone, naltrexone, noroxymorphone, oxymorphone and nalbuphone are particularly targeted.

The expression "α,β-unsaturated compounds" is understood to mean compounds comprising a double bond in the 7 and 8 positions of the morphine ring conjugated with a ketone in the 6 position. More specifically, they are 3-hydroxy-7,8-didehydromorphinone derivatives corresponding to the following formula (II):

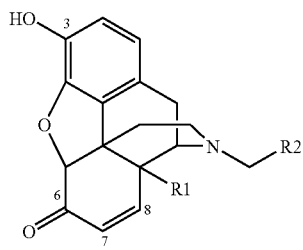

(II)

in which:
R1 and R2 have the same meanings as indicated above.

The expression "product of Michael addition to the α,β-unsaturated compound" is understood to mean the corresponding saturated hydroxylated compound. More specifically, they are 3,8-dihydroxymorphinone derivatives corresponding to the following formula (III):

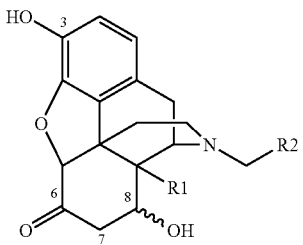

(III)

in which:
R1 and R2 have the same meanings as indicated above.

The expression "crude morphine compound" is understood to mean a mixture of compounds essentially comprising a morphine compound or 3-hydroxymorphinone derivative as defined above and generally an α,β-unsaturated compound or 3-hydroxy-7,8-didehydromorphinone derivative as defined above in a smaller amount.

In this mixture, the content of α,β-unsaturated compound is generally less than 1% by weight and most often between 0.1% and 0.2% by weight.

The expression "product resulting from the aldol condensation reaction" is understood to mean the dimer resulting from the reaction of the enolate with the ketone. More specifically, they are bishydroxymorphinol-morphinone derivatives corresponding to the following formula (IV):

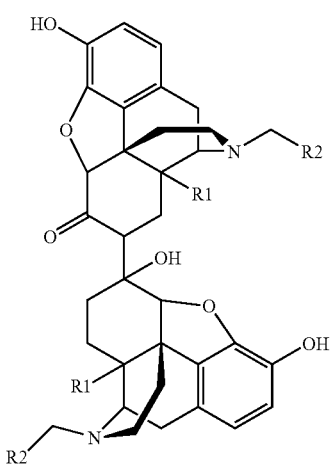

(IV)

in which:
R1 and R2 have the same meanings as indicated above.

The expression "product resulting from the crotonization reaction" is understood to mean the dimer resulting from the dehydration reaction of the aldol. More specifically, they are bishydroxymorphinene-morphinone derivatives corresponding to the following formula (V):

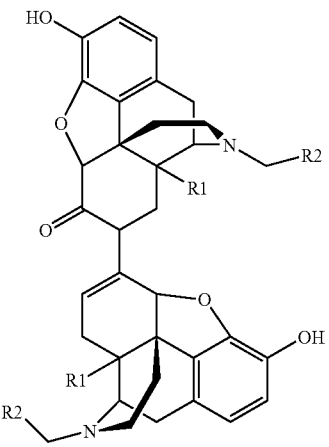

(V)

in which:
R1 and R2 have the same meanings as indicated above.

The invention is based on the surprising observation that the content of α,β-unsaturated compounds, in particular those comprising a double bond in the 7 and 8 positions of the morphine ring conjugated to a ketone in the 6 position, in morphine compounds can be reduced by addition of Michael type of the hydroxide ion to the double bond.

Process

Consequently, according to a first aspect, the invention is targeted at a process for the preparation of morphine compounds comprising a low content of α,β-unsaturated compounds, comprising the stages of:

(i) bringing the crude morphine compound into contact with a base under conditions which make possible the Michael addition reaction on the α,β-unsaturated compound(s) present;

(ii) separating the morphine compound from the reaction mixture; and (iii) if appropriate, separating the addition product formed from the morphine compound.

Advantageously, the process additionally comprises the subsequent stage of:

(iv) converting the morphine compound to a corresponding pharmaceutically acceptable salt, in particular to the hydrochloride.

The conditions which make possible the Michael reaction of stage (i), in particular the temperature and time conditions, can vary according to the morphine compound treated. These conditions can be easily determined by a person skilled in the art using routine techniques. The temperature and time conditions relating to the treatment of naloxone are given below by way of illustration.

Preferably, stage (i) of the process described is carried out:
by introducing the crude morphine compound into the base;
at a temperature of 20 to 25° C.;
with a contact time of less than one hour; and/or
in a medium exhibiting a pH of greater than 13, advantageously of greater than 14.

Preferably, stage (ii) is carried out by precipitation, which is advantageously obtained by addition of a neutralizing agent, in particular an acid.

Stage (iii) is preferably carried out at the same time as stage (iv).

According to a preferred embodiment of the process, the morphine compound is naloxone. Preferably, the α,β-unsaturated compound is 7,8-didehydronaloxone.

The process according to the invention makes it possible, by simple and rapid treatment involving standard and non-toxic reactants, to obtain a morphine compound of very high purity. The process makes it possible in particular to lower the presence of α,β-unsaturated compounds below regulatory thresholds and generally below the detection threshold.

The addition compounds formed are hydrophilic and can for this reason be easily removed. Advantageously, this removal takes place during the usual purification and in particular during the conversion to a pharmaceutically acceptable salt, for example during hydrochlorination. The purification can in particular comprise a stage of filtration, for example through alumina.

The process described can thus be employed without major modifications to current and registered procedures.

The process described makes it possible to convert undesirable α,β-unsaturated compounds by a nucleophilic addition reaction known as Michael-type addition. This reaction is well known as such and is described, for example, in "Advanced Organic Chemistry" by Smith and March, 5th Edition, (Chapter 15, pp. 976, 1022-1024).

The addition takes place on the double bond conjugated with the ketone functional group. The addition product formed is thus the corresponding hydroxylated saturated compound. These compounds are generally less toxic than the α,β-unsaturated compounds.

Reaction Scheme 1 below illustrates the reaction forming the basis of the process for this specific example of naloxone. Naloxone can comprise, as α,β-unsaturated impurity, in particular 7,8-didehydronaloxone. This compound is converted to 8-hydroxynaloxone by base treatment.

Reaction Scheme 1: Michael-type addition to 7,8-didehydronaloxone

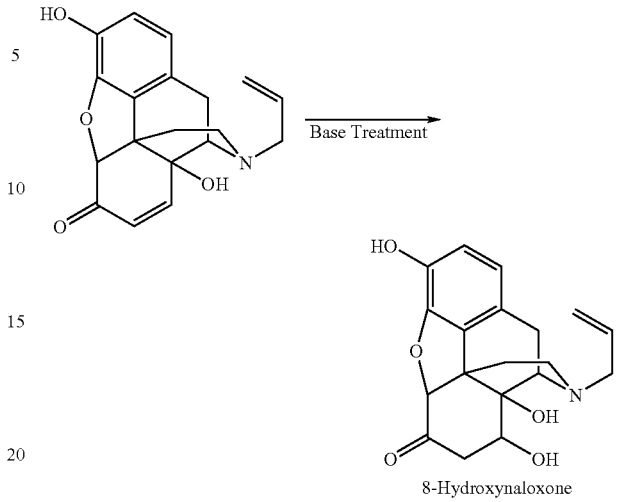

8-Hydroxynaloxone

Due to the presence of an additional hydroxyl group, the compound formed by the reaction is more hydrophilic and can, if appropriate, be easily separated from the morphine compound.

According to a specific embodiment, the compounds formed by the Michael-type addition reaction are separated during the usual subsequent stages of isolation and of purification.

The Michael-type addition reaction takes place in competition with secondary reactions, in particular the aldol condensation and crotonization reaction.

The aldol condensation reaction is illustrated in Reaction Scheme 2 below for the example of naloxone. The dimeric product formed is relatively hydrophilic. It can for this reason be easily separated during subsequent stages of isolation and of purification.

Reaction Scheme 2: Aldol condensation of naloxone

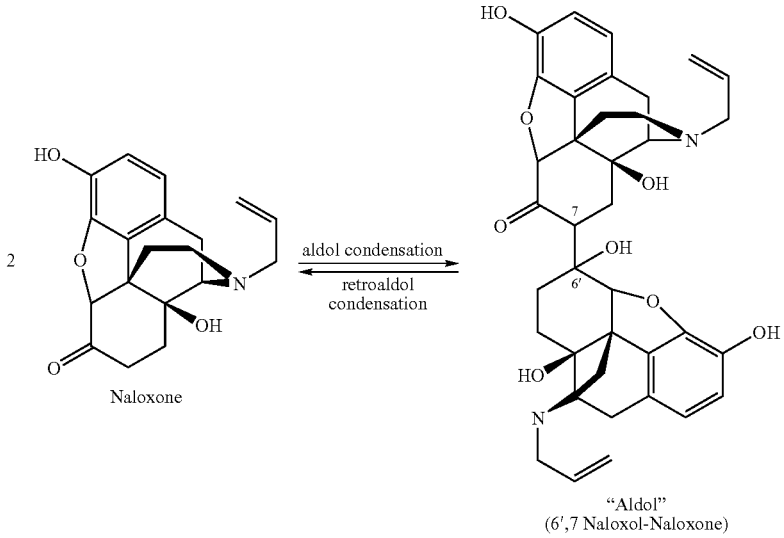

"Aldol"
(6',7 Naloxol-Naloxone)

Reaction Scheme 3: Crotonization of naloxone

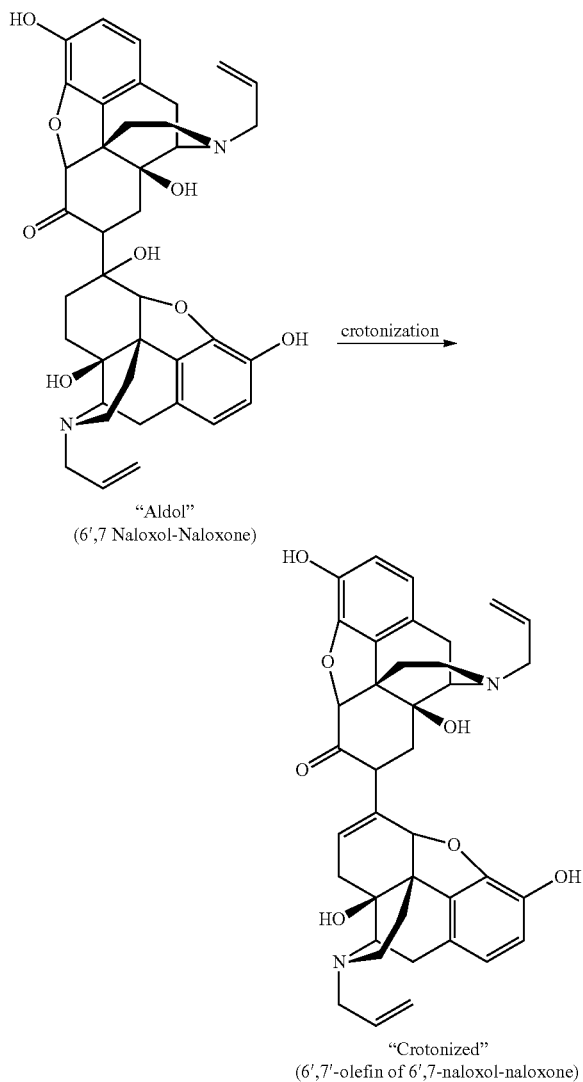

"Aldol"
(6',7 Naloxol-Naloxone)

"Crotonized"
(6',7'-olefin of 6',7-naloxol-naloxone)

The crotonization of naloxone results in the corresponding dehydrated compound. The reaction is illustrated in Reaction Scheme 3 above for the example of naloxone. It has been established by structural NMR analysis that only the compound with endocyclic unsaturation is formed.

Crotonization is an irreversible reaction, in contrast to the aldol condensation reaction, which is in equilibrium with the reverse reaction, known as retroaldol condensation. Furthermore, the compound resulting from the crotonization of the aldol product is not very soluble in water and is for this reason more difficult to separate from the reaction product.

Surprisingly, it has been found that it is possible to limit the impact of the secondary reactions by appropriately selecting certain parameters of the process.

In particular, it proved to be the case that an effective means for limiting the crotonization reaction is that of limiting the formation of aldol, which is the starting material for the crotonization.

In point of fact, it has been found that the aldol condensation reaction is disadvantaged at low temperature, in a highly basic medium, and with short contact times.

Consequently, it is preferable to carry out the reaction at low temperature. However, it has been observed that the Michael addition is slow when the temperature is too low.

A reaction temperature from 10 to 40° C., in particular from 20 to 25° C., generally constitutes a good compromise. It is particularly preferred to carry out the reaction at ambient temperature, without heating or cooling means.

The specific stage described is carried out on the crude morphine compound accessible by one of the known conventional processes, for example described in "Chemistry of the Opium Alkaloids" by Lyndon F. Small and Robert E. Lutz, Supplement No. 108 to the Public Health Reports, US Government Printing Office, 1982.

The crude morphine compound obtained by these processes generally exhibits a content of α,β-unsaturated compounds of less than 1% by weight, generally between 0.1% and 0.2% by weight.

The process according to the invention makes possible the Michael-type addition reaction on α,β-unsaturated compounds present in the crude morphine compound.

The crude morphine compound is generally dissolved in an appropriate solvent, advantageously in aqueous solution. It is preferable for the solution to exhibit a concentration of crude morphine compound of between 5 and 25% by weight.

The base used is preferably a strong inorganic base, such as alkali metal hydroxides and alkaline-earth metal hydroxides, in particular sodium hydroxide or potassium hydroxide.

The amount of base is preferably in excess with respect to the morphine compound involved. Generally, it represents at least 3 equivalents, indeed even at least 5 equivalents, calculated with respect to the morphine compound. Preferably, the reaction mixture exhibits a pH of greater than 13 or even of greater than 14. Use will thus preferably be made of a base in concentrated solution.

This is because the retroaldol condensation reaction is favoured in a strongly basic medium, which limits the amount of aldol available for crotonization.

According to a preferred embodiment, the solution of morphine compound is introduced into the base and not the reverse. This alternative form, known as reverse pouring, provides a reaction medium which is strongly basic at all times.

The process according to the invention can be carried out simply and on conventional equipment.

The morphine compound is brought into contact with a basic medium, preferably with stirring. The reaction medium is preferably maintained at a temperature from 20 to 25° C.

The contact time of the reaction mixture is preferably short in order to place the aldol condensation at a disadvantage. This does not present a problem in terms of conversion as the Michael addition reaction is generally complete in 10 to 40 minutes and most often in 20 to 30 minutes.

On conclusion of the reaction, generally after less than one hour, the reaction medium is neutralized. In order to limit the rise in temperature and thus crotonization reactions, it is preferable to neutralize the reaction mixture by gradual addition of a neutralizing agent.

The neutralizing agent will generally be an ordinary acid which is strong or weak and organic or inorganic. Hydrochloric acid, sulphuric acid or acetic acid are particularly preferred. Neutralization is carried out until the morphine compound precipitates. Generally, the morphine product precipitates at neutral or moderately basic pH, for example of between pH 8 and 10.

The solid product is subsequently separated from the reaction mixture by conventional methods, for example by filtration.

Filtration through a polar medium, such as alumina, is particularly advantageous as it makes possible retention by affinity of the more hydroxylated compounds, in particular the aldol condensation products.

Generally, the morphine compound obtained, in the solvated base form, is subsequently converted to a pharmaceutically acceptable salt, in particular to the hydrochloride, mucate, hydrobromide, stearate, pamoate, napsylate, 2-hydroxy-5-(1,1,3,3-tetramethylbutyl)benzoate or 3,5-bis(1,1-dimethylethyl)-2,6-dihydroxybenzoate.

This stage can be carried out by reaction of the morphine compound obtained with the corresponding acid. Generally, the base is not very soluble in water and a solution of the morphine compound is thus prepared in an appropriate solvent, for example acetone. After addition of the acid, the salt formed is separated, for example by precipitation.

The salts of the dimeric compounds resulting from the aldol condensation and crotonization reactions are more soluble in water than the salt of the morphine compound. Their content can thus be reduced during this stage.

The morphine compound or its salt thus obtained can, if necessary, be further purified according to known methods, for example by recrystallization.

Furthermore, it is possible to obtain the anhydrous morphine compound by removal of the solvent, in particular by drying in an oven.

According to an advantageous aspect of the invention, the compounds resulting from the reaction and from the secondary reactions are thus separated by the subsequent purification stages, without requiring a stage especially provided for this purpose.

Composition

According to a second aspect, the invention relates to a composition comprising at least 99% by dry weight of morphine compound and a content of $\alpha,\beta$-unsaturated compound of less than 100 ppm. In particular, the invention relates to a composition comprising at least 99%, preferably at least 99.5%, by dry weight of morphine compound or one of its pharmaceutically acceptable salts and an $\alpha,\beta$-unsaturated compound in a content of less than 100 ppm, preferably of less than 50 ppm and more preferably of less than 25 ppm.

The morphine compounds and their salts readily form solvates, in particular in the form of mono-, di- or trihydrates. The contents of these compounds are thus generally expressed with respect to the dry compound, without taking into account the content of water or of solvents. The contents shown subsequently, unless otherwise indicated, are thus always understood with respect to the dry compound.

Such compositions are particularly targeted when the morphine compound is naloxone, its hydrochloride or also the hydrochloride dihydrate. In these compositions, the $\alpha,\beta$-unsaturated compound is preferably 7,8-didehydronaloxone.

According to a specific embodiment, the composition furthermore comprises, in a small amount, compounds resulting from the aldol condensation reaction and crotonization reaction.

Thus, a particular subject-matter of the present invention is a composition comprising at least 99% by dry weight, preferably at least 99.5% by dry weight, of a morphine compound or of one of its pharmaceutically acceptable salts and an $\alpha,\beta$-unsaturated compound in a content of less than 100 ppm and preferably less than 50 ppm, and additionally comprising at least one compound resulting from the aldol condensation and crotonization reactions.

These compounds resulting from the aldol condensation and crotonization reactions no longer exhibit a potential risk of genotoxicity associated with $\alpha,\beta$-unsaturated ketone structures.

The compounds resulting from the aldol condensation reaction and from the crotonization reaction are generally present in a content of less than 1000 ppm and in particular of less than or equal to 500 ppm in the compositions according to the invention.

When, in the composition according to the invention the morphine compound is in salt form, the compound resulting from the aldol condensation reaction is generally present in a content ranging from 20 to 200 ppm and in particular from 50 to 150 ppm.

When, in the composition according to the invention, the morphine content is in salt form, the compound resulting from the crotonization reaction is generally present in a content ranging from 150 to 500 ppm and in particular from 200 to 350 ppm.

As regards the naloxone, it is 6',7-naloxol-naloxone and the corresponding 6',7'-olefin.

The compositions according to the invention comprising a pharmaceutically acceptable salt of the morphine compound, in particular a naloxone hydrochloride, are particularly preferred. The morphine compounds or their salts are generally solvates and in particular hydrates. A composition comprising naloxone hydrochloride dihydrate is particularly targeted. In particular, the present invention is targeted at a composition comprising naloxone hydrochloride dihydrate, 7,8-didehydronaloxone, in particular in a content of less than 90 ppm, 6',7-naloxol-naloxone, in particular in a content ranging from 50 to 150 ppm, and the 6',7-olefin of 6',7-naloxol-naloxone, in particular in a content ranging from 200 to 350 ppm.

When the morphine compound is in the solvate form, the composition will additionally comprise a corresponding amount of the solvent. For the case of naloxone hydrochloride dihydrate, the composition can additionally comprise up to 10% by weight of water, with respect to the total weight of the composition.

The invention will be explained in more detail using the following examples and the figures, which show:

BREIF DESCRIPTION OF THE DRAWINGS

Figure 2:
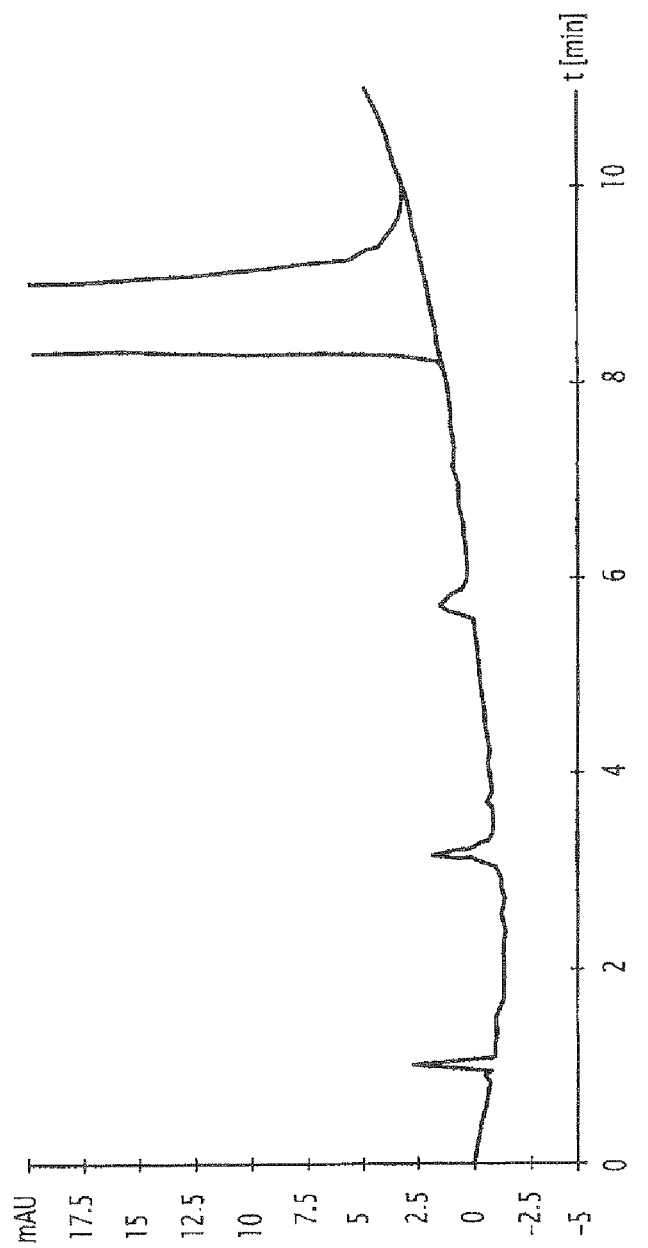

FIG. 1: Result of analysis by HPLC of naloxone base comprising a low content of $\alpha,\beta$-unsaturated compounds obtained in the example; and FIG. 2: Result of analysis by HPLC of naloxone hydrochloride comprising a low content of $\alpha,\beta$-unsaturated compounds obtained in the example.

EXAMPLES

Example

Preparation of Naloxone Comprising a Low Content of $\alpha,\beta$-Unsaturated Compounds 15.08 g (0.046 mol) of crude naloxone base, obtained by N-allylation of noroxymorphone hydrochloride in dimethylformamide by allyl bromide in the presence of $NaHCO_3$ at 60° C., followed by precipitation from water, are introduced into a 250-ml three-necked flask equipped with a thermometer and a magnetic bar, followed by 105 ml of water and 9 ml (0.06 mol, 2 eq) of concentrated sodium hydroxide solution (30%). The medium is stirred at ambient temperature until completely dissolved.

The medium is subsequently charged to a dropping funnel and then added dropwise to a three-necked flask comprising 36 ml (0.27 mol; 8 eq) of concentrated sodium hydroxide solution (30%). The initial ambient temperature of 21.6° C. of the reaction medium reaches 21.5° C. at the end of the addition, the pH of the reaction medium then being 14.4.

Stirring is maintained at this temperature for a further 30 minutes. 39 ml (0.37 mol; 8.2 eq) of concentrated hydrochloric acid (37%) are subsequently added dropwise in order to minimize the rise in the temperature.

At the end of the addition, the reaction medium exhibits a temperature of 41.7° C. and a pH of 9. The medium is cooled to 10° C. and the precipitate is separated by filtration through a sintered glass funnel. The solid product separated is dried in a ventilated oven at 60° C. The crude naloxone base treated is isolated with a dry weight of 15.64 g. The product obtained on conclusion of these operations is called "treated naloxone base" in Tables 1 to 4 below.

The product obtained is subsequently dissolved in acetone, filtered through alumina and recrystallized from toluene. The product obtained on conclusion of these operations is called "pure naloxone base" in Tables 1 to 4 below.

The naloxone base obtained is dissolved in acetone and then converted to the hydrochloride by addition of concentrated hydrochloric acid. The hydrochloride is precipitated by cooling, filtered off and dried. The product obtained on conclusion of these operations is called "pure naloxone hydrochloride" in Tables 1 to 4 below.

The product obtained is analysed according to the HPLC method described in the European Pharmacopoeia after the base treatment and after conversion to the hydrochloride.

The test is repeated twice according to the same procedure. The results of the analyses are collated in the following Tables 1 and 2.

It is noticed that the process according to the invention makes it possible to obtain, by the base treatment, naloxone comprising a low content of 7,8-didehydronaloxone. Specifically, the treatment makes it possible to lower the 7,8-didehydronaloxone content from 0.8% by weight initially to less than 0.03% by weight, thus below the detection threshold. A more specific HPLC method makes it possible to record that the 7,8-didehydronaloxone content, which has to be less than 100 ppm, exhibits a usual value from 60 to 90 ppm.

The naloxone thus obtained therefore corresponds at this stage to the regulatory requirements as regards the 7,8-didehydronaloxone content.

Furthermore, the appearance is noted, after treatment of the naloxone, of the addition product 8-hydroxynaloxone and also of small amounts of the products from the competing aldol condensation and crotonization reactions. However, these compounds are very largely removed during the subsequent stages of purification and of conversion to the hydrochloride.

The results of the HPLC analyses of Tables 1 and 2, treated according to more precise quantification methods, lead to the values presented respectively in the following Tables 3 and 4.

TABLE 1

HPLC Analysis Test 1

| | Didehydronaloxone | | 8-Hydroxy-naloxone | Aldol | Crotonized |
|---|---|---|---|---|---|
| | (%)+ | (ppm)* | (%)+ | (%)+ | (%)+ |
| Crude naloxone base | 0.08 | 473 | — | — | — |
| Treated naloxone base | ≤0.03 | 95 | 0.04 | ≤0.03 | 0.05 |
| Pure naloxone base | ≤0.03 | 85 | ≤0.03 | ≤0.03 | 0.04 |
| Pure naloxone hydrochloride | ≤0.03 | 63 | ≤0.03 | ≤0.03 | ≤0.03 |

+HPLC method for the quantification of 7,8-didehydronaloxone according to the European Pharmacopoeia;
*HPLC evaluation method devoted to the precise quantification of 7,8-didehydronaloxone.
The difference between the two values is due in particular to a difference in response factor in the European Pharmacopoeia.

TABLE 2

HPLC Analysis Test 2

| | Didehydronaloxone | | 8-Hydroxy-naloxone | Aldol | Crotonized |
|---|---|---|---|---|---|
| | (%)+ | (ppm)* | (%) | (%) | (%) |
| Crude naloxone base | 0.07 | 400 | — | — | — |
| Treated naloxone base | ≤0.03 | 64 | 0.04 | ≤0.03 | 0.05 |
| Pure naloxone base | ≤0.03 | 83 | ≤0.03 | ≤0.03 | 0.04 |
| Pure naloxone hydrochloride | ≤0.03 | 59 | ≤0.03 | ≤0.03 | ≤0.03 |

+HPLC method for the quantification of 7,8-didehydronaloxone according to the European Pharmacopoeia;
*HPLC evaluation method devoted to the precise quantification of 7,8-didehydronaloxone.
The difference between the two values is due in particular to a difference in response factor in the European Pharmacopoeia.

TABLE 3

HPLC analysis with different quantification method from Test 1

| | Didehydronaloxone | | 8-Hydroxy-naloxone | Aldol | Crotonized |
|---|---|---|---|---|---|
| | (%)+ | (ppm)* | (ppm) | (ppm) | (ppm) |
| Crude naloxone base | 0.08 | 473 | n.d. | n.d. | n.d. |
| Treated naloxone base | ≤0.03 | 95 | 400 | 200 | 500 |
| Pure naloxone base | ≤0.03 | 85 | 300 | 100 | 400 |
| Pure naloxone hydrochloride | ≤0.03 | 63 | 200 | 95 | 300 |

+HPLC method for the quantification of 7,8-didehydronaloxone according to the European Pharmacopoeia;
*HPLC evaluation method devoted to the precise quantification of 7,8-didehydronaloxone.
The difference between the two values is due in particular to a difference in response factor in the European Pharmacopoeia.

TABLE 4

HPLC analysis with different quantification method from Test 2

| | Didehydronaloxone | | 8-Hydroxy-naloxone | Aldol | Crotonized |
|---|---|---|---|---|---|
| | (%)+ | (ppm)* | (ppm) | (ppm) | (ppm) |
| Crude naloxone base | 0.07 | 400 | n.d. | n.d. | n.d. |
| Treated naloxone base | ≦0.03 | 64 | 400 | 200 | 400 |
| Pure naloxone base | ≦0.03 | 83 | 210 | 91 | 400 |
| Pure naloxone hydrochloride | ≦0.03 | 59 | 150 | 76 | 250 |

+HPLC method for the quantification of 7,8-didehydronaloxone according to the European Pharmacopoeia;
*HPLC evaluation method devoted to the precise quantification of 7,8-didehydronaloxone. The difference between the two values is due in particular to a difference in response factor in the European Pharmacopoeia.

What is claimed is:

1. A process for the preparation of morphine compounds of the formula (I):

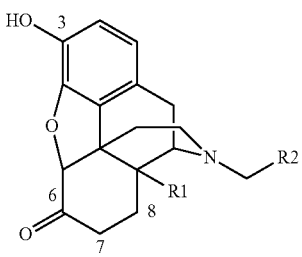

(I)

wherein:
R1 is selected from the group consisting of a hydrogen atom and a hydroxyl group;
and R2 is selected from the group consisting of a hydrogen atom, $(C_1-C_6)$alkyl group, cyclo$(C_3-C_6)$alkyl group and $(C_2-C_6)$alkenyl group;
comprising a low content of α,β-unsaturated compounds, comprising the stages of:
(i) bringing the crude morphine compound into contact with a base, at a pH of greater than 13, under conditions which make possible the Michael addition reaction on the α,β-unsaturated compound(s) present;
(ii) separating the morphine compound from the reaction mixture; and
(iii) if appropriate, separating the addition product formed from the morphine compound.

2. The process according to claim 1, comprising, as subsequent stage:
(iv) converting the morphine compound to a corresponding pharmaceutically acceptable salt.

3. The process according to claim 1, in which stage (i) is carried out by introducing the crude morphine compound into the base.

4. The process according to claim 1, in which in stage (ii) the morphine product is separated by precipitation by addition of a neutralizing agent.

5. The process according to claim 2, in which stage (iii) is carried out at the same time as stage (iv).

6. The process according to claim 1, in which the morphine compound is naloxone and the α,β-unsaturated compound is 7,8-didehydronaloxone.

7. The process according to claim 2, in which the morphine compound is naloxone and the α,β-unsaturated compound is 7,8-didehydronaloxone.

8. The process according to claim 6, in which stage (i) is carried out at a temperature of 20 to 25° C.

9. The process according to claim 6, in which stage (i) is carried out with a contact time of less than one hour.

10. A composition comprising at least 99% by dry weight of a morphine compound of the formula (I);

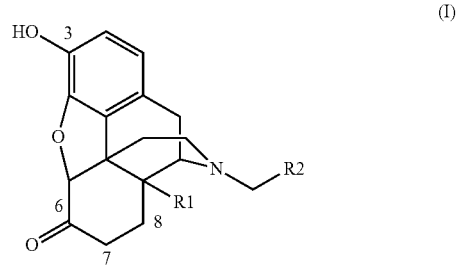

(I)

wherein:
R1 is selected from the group consisting of a hydrogen atom and a hydroxyl group;
and R2 is selected from the group consisting of a hydrogen atom, $(C_1-C_6)$alkyl group, cyclo$(C_3-C_6)$alkyl group and $(C_2-C_6)$alkenyl group;
or a pharmaceutically acceptable salt thereof and an α,β-unsaturated compound in a content of less than 100 ppm and additionally comprising at least one compound resulting from an aldol condensation or crotonization reaction.

11. The composition according to claim 10, comprising at least 99.5% by dry weight of morphine compound or a pharmaceutically acceptable salt thereof.

12. The composition according to claim 10, which contains less than 50 ppm of α,β-unsaturated compound.

13. The composition according to claim 10, in which the content of the compound resulting from the aldol condensation reaction is less than 1000 ppm.

14. The composition according to claim 10, in which the content of the compound resulting from the crotonization reaction is less than 1000 ppm.

15. The composition according to claim 10, in which the morphine compound is naloxone and the α,β-unsaturated compound is 7,8-didehydronaloxone.

16. The composition according to claim 10, in which the pharmaceutically acceptable salt of the morphine compound is naloxone hydrochloride and the α,β-unsaturated compound is 7,8-didehydronaloxone.

17. The composition according to claim 10, in which the pharmaceutically acceptable salt of the morphine compound is naloxone hydrochloride dihydrate and the α,β-unsaturated compound is 7,8-didehydronaloxone.

18. The composition according to claim 15, additionally comprising 6',7-naloxol-naloxone.

19. The composition according to claim 15, additionally comprising the 6',7'-olefin of 6',7-naloxol-naloxone.

* * * * *